US00PP35747P2

(12) United States Plant Patent
Gardner et al.

(10) Patent No.: US PP35,747 P2
(45) Date of Patent: Apr. 16, 2024

(54) PEACH TREE NAMED 'SPRING BREEZE'

(50) Latin Name: *Prunus persica*
Varietal Denomination: Spring Breeze

(71) Applicants: Lacey Marie Gardner, Modesto, CA (US); Jalen Robert Zaiger, Modesto, CA (US); Tracee Louise Bettencourt, Modesto, CA (US)

(72) Inventors: Lacey Marie Gardner, Modesto, CA (US); Jalen Robert Zaiger, Modesto, CA (US); Tracee Louise Bettencourt, Modesto, CA (US)

( * ) Notice: Subject to any disclaimer, the term of this patent is extended or adjusted under 35 U.S.C. 154(b) by 0 days.

(21) Appl. No.: 17/803,743

(22) Filed: Nov. 8, 2022

(51) Int. Cl.
*A01H 6/74* (2018.01)
*A01H 5/08* (2018.01)

(52) U.S. Cl.
USPC ..... Plt./197

(58) Field of Classification Search
USPC ..... Plt./156, 194, 197
See application file for complete search history.

*Primary Examiner* — Karen M Redden

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium to large size fruit.
3. Clingstone fruit with firm, yellow flesh.
4. Fruit with very good flavor and eating quality.
5. Fruit having an attractive red skin color.

1 Drawing Sheet

Botanical designation: *Prunus persica.*
Variety denomination: 'Spring Breeze'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, California.

Prior Varieties

Among the existing varieties of peach trees, which are known to us, and mentioned herein, 'Zee Pride' Peach (U.S. Plant Pat. No. 22,606), 'Vista' Peach (U.S. Plant Pat. No. 9,549) and the proprietary non-patented peach seedling selections '280B014' and '53ZM62'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, California as an open pollinated seedling selection from the proprietary non-patented peach seedling '280BC14'. The seed parent (280BC14) originated from a cross between 'Vista' Peach (U.S. Plant Pat. No. 9,549) and the proprietary non-patented peach seedling selection '53ZM62'. A large number of these open pollinated seedlings were planted and maintained on their own root system. Under close and careful observation we recognized the desirable tree and fruit characteristics of the present seedling and selected it in 2017 for additional asexual propagation and commercialization.

ASEXUAL REPRODUCTION OF THE VARIETY

In 2017 asexual reproduction of the new and distinct variety of peach tree was by budding to 'Nemaguard' Rootstock (non-patented), as performed by us in our experimental orchard located near Modesto, California, and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of medium to large size, yellow flesh, clingstone fruit. The fruit is further characterized by its attractive red skin color and having good storage and shipping ability. In comparison to its proprietary non-patented seed parent '280B014' the fruit of the new variety is larger in size and has a better flavor and eating quality. In comparison to the commercial variety 'Zee Pride' Peach (U.S. Plant Pat. No. 22,606) the fruit of the new variety is 26 days earlier in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, California, with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters in height the first growing season. Varies with cultural practices, soil type, fertility and climatic conditions.

*Form*.—Upright, usually pruned to vase shape.

*Branching habit*.—Upright, crotch angle approximately 25°, increases with heavy crop load.

*Productivity*.—Productive, thinning and spacing of fruit desirable for marketable size. Fruit set varies with climatic conditions during bloom time.

*Bearer*.—Regular, has had adequate fruit set 4 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement 150 hours at or below 45° F.

Trunk:

*Size*.—Large, average circumference 25.4 cm at 22.9 cm above ground on a 5 year old tree.

*Stocky*.—Medium stocky.

*Texture*.—Medium shaggy, roughness increases with age.

*Color*.—Varies from 5YR 5/4 to 5YR 3/4.

Branches:

*Size*.—Medium. Average circumference 10.4 cm at 1.2 meters above ground. Crotch angle approximately 25°, increases with heavy crop load.

*Surface texture*.—New growth relatively smooth. Mature growth medium rough, roughness increases with age.

*Lenticels*.—Average number 23 in a 25.8 square cm area. Average length 4.2 mm. Average width 2.1 mm. Color 5YR 5/8.

*Color*.—New growth varies from 5GY 7/6 to 5GY 6/6. Mature growth varies from 5YR 5/4 to 5YR 3/4, varies with age of growth.

Leaves:

*Size*.—Medium. Average length 135.0 mm. Average width 33.8 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 9.2 mm. Average width 1.6 mm. Longitudinally grooved. Surface — glabrous. Color varies from 5GY 6/4 to 5GY 6/6.

*Glands*.—Type — reniform. Size — small. Average length 0.1 mm. Average diameter 0.1 mm. Number varies from 2 to 4, average number 4. Located primarily on base of leaf blade and upper portion of petiole. Color varies from 5GY 5/6 to 5GY 6/6.

*Stipules*.—None present at time of measurement.

*Color*.—Upper surface varies from 4GY 4/4 to 7.5GY 4/4. Lower surface varies from 5GY 5/4 to 5GY 4/4. Midvein color varies from 5GY 6/4 to 5GY 7/4.

Flower buds:

*Size*.—Large. Average length 16.4 mm. Average diameter 11.0 mm.

*Hardiness*.—Hardy with respect to California winters.

*Density*.—Medium dense.

*Form*.—Elongated.

*Pedicel*.—Average length 4.7 mm. Average width 1.2 mm. Surface — glabrous. Color varies from 5GY 5/6 to 7.5R 2/6.

*Color*.—Varies from 5RP 7/10 to 5RP 8/4.

Flowers:

*Blooming period*.—Date of First Bloom Feb. 3, 2022. Date of Petal Fall Feb. 13, 2022, varies slightly with climatic conditions.

*Size*.—Large. Average height 19.2 mm. Average diameter 40.1 mm.

*Petals*.—Normally 5, alternately arranged to sepals. Size — large. Average length 22.3 mm. Average diameter 18.4 mm. Petal apex — rounded. Petal base- truncate. Form — elliptical. Arrangement — overlapping. Margin — entire. Color varies from 2.5RP 8/4 to 5RP 8/4, fades with age of flower.

*Sepals*.—Normally five, alternately arranged to petals. Size — large. Average length 5.6 mm. Average width 5.8 mm. Sepal apex — triangular to ovate. Shape — triangular. Margin — entire. Surface — upper surface glabrous, lower surface pubescent. Color — upper surface varies from 5GY 4/8 to 7.5R 3/6. Lower surface varies from 5R 2/4 to 7.5R 2/4.

*Stamens*.—Average number per flower 42. Average filament length 14.8 mm. On average, the stamens are even with the height of the petals. Filament color varies from N 9.5/(white) to 5RP 8/4. Anther color varies from 7.5R 4/12 to 5Y 9/6.

*Pollen*.—Self-fertile. Color varies from 5Y 8/10 to 5Y 7/10.

*Pistil*.—Number — normally one. Average length 17.2 mm. Position of stigma an average of 1.2 mm below anthers. Surface — pubescent. Color varies from 7.5Y 8.5/6 to 10Y 8/6.

*Fragrance*.—Slight.

*Color*.—Varies from 5RP 9/2 to 7.5RP 9/2.

*Pedicel*.—Average length 5.7 mm. Average width 1.3 mm. Color varies from 5GY 5/6 to 7.5R 2/6.

*Number flowers per flower bud*.—Normally one.

Fruit:

*Maturity when described*.—Firm ripe and ready for consumption.

*Date of first picking*.—May 10, 2022.

*Date of last picking*.—May 20, 2022, varies slightly with climatic conditions.

*Size*.—Medium to large. Average diameter axially 62.5 mm. Average transversely in suture plane 68.8 mm. Average weight 178.9 grams, varies slightly with fertility of the soil, amount of thinning and climatic conditions.

*Form*.—Globose.

*Suture*.—Slightly lipped, extends from base to apex.

*Ventral surface*.—Slightly lipped.

*Apex*.—Rounded to slight tip.

*Base*.—Retuse.

*Stem cavity*.—Rounded to slightly elongated in suture plane. Average depth 7.3 mm. Average diameter 9.0 mm.

Stem:

*Size*.—Medium. Average length 10.8 mm. Average diameter 3.4 mm.

*Color*.—Varies from 2.5GY 6/8 to 5GY 7/6.

Flesh:

*Ripens*.—Evenly.

*Texture*.—Firm, meaty, slightly crisp.

*Fibers*.—Few, small, tender.

*Firmness*.—Firm, comparable to other commercial peach varieties.

*Aroma*.—Moderate.

*Amydgalin*.—Undetected.

*Eating quality*.—Very good.

*Flavor*.—Good, with a good balance between acid and sugar.

*Juice*.—Moderate amount, enhances flavor.

*Acidity*.—Not available.

*Brix*.—Average Brix 13.0°, varies slightly with amount of fruit per tree and climatic conditions.

*Color*.—Varies from 5Y 8/8 to 5Y 7/8.

*Pit cavity*.—Average length 36.0 mm. Average width 29.0 mm. Average depth 14.0 mm. Color varies from 2.5Y 7/12 to 2.5Y 7/10.

Skin:

*Thickness*.—Medium.

*Surface*.—Smooth.

*Pubescence*.—Moderate amount, short in length.

*Tendency to crack*.—None.

*Color*.—Ground color varies from 5Y 8.5/6 to 5Y 8/6. Overspread with 5R 4/8 to 5R 4/10.

*Tenacity*.—Tenacious to flesh.

*Astringency*.—Slight to none.

Stone:

*Type*.—Clingstone, strong adherence to flesh.

*Size*.—Large. Average length 35.0 mm. Average width 28.0 mm. Average depth 27.0 mm.

*Form*.—Obovoid.

*Base*.—Flat.

*Apex*.—Rounded.

*Surface*.—Pitted throughout, pits vary from rounded to slightly elongated.

*Sides*.—Unequal, one side extending further from suture plane.

*Ridges*.—Relatively smooth, narrow ridges extending from base to apex.

*Tendency to split*.—Slight.

*Color*.—Varies from 2.5Y 7/6 to 2.5Y 7/8 when dry.

Kernel:

*Size*.—Medium. Average length 18.6 mm. Average width 11.0 mm. Average depth 8.1 mm.

*Form*.—Ovate.

*Viability*.—Partially viable, incomplete embryo development.

*Skin color*.—Varies from 5Y 9/4 to 5Y 9/6.

Use:

*Dessert*.—Market — local and long distance.

Keeping quality: Good, held firm in cold storage for 2 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, California, no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers foliage and fruit herein described may vary in slight detail due to climate, soil conditions and cultural practices under which the variety may be grown. The present description is that of the variety grown under the ecological conditions prevailing near Modesto, California.

The invention claimed is:

1. A new and distinct variety of peach tree (*Prunus persica*) 'Spring Breeze', substantially as illustrated and described.

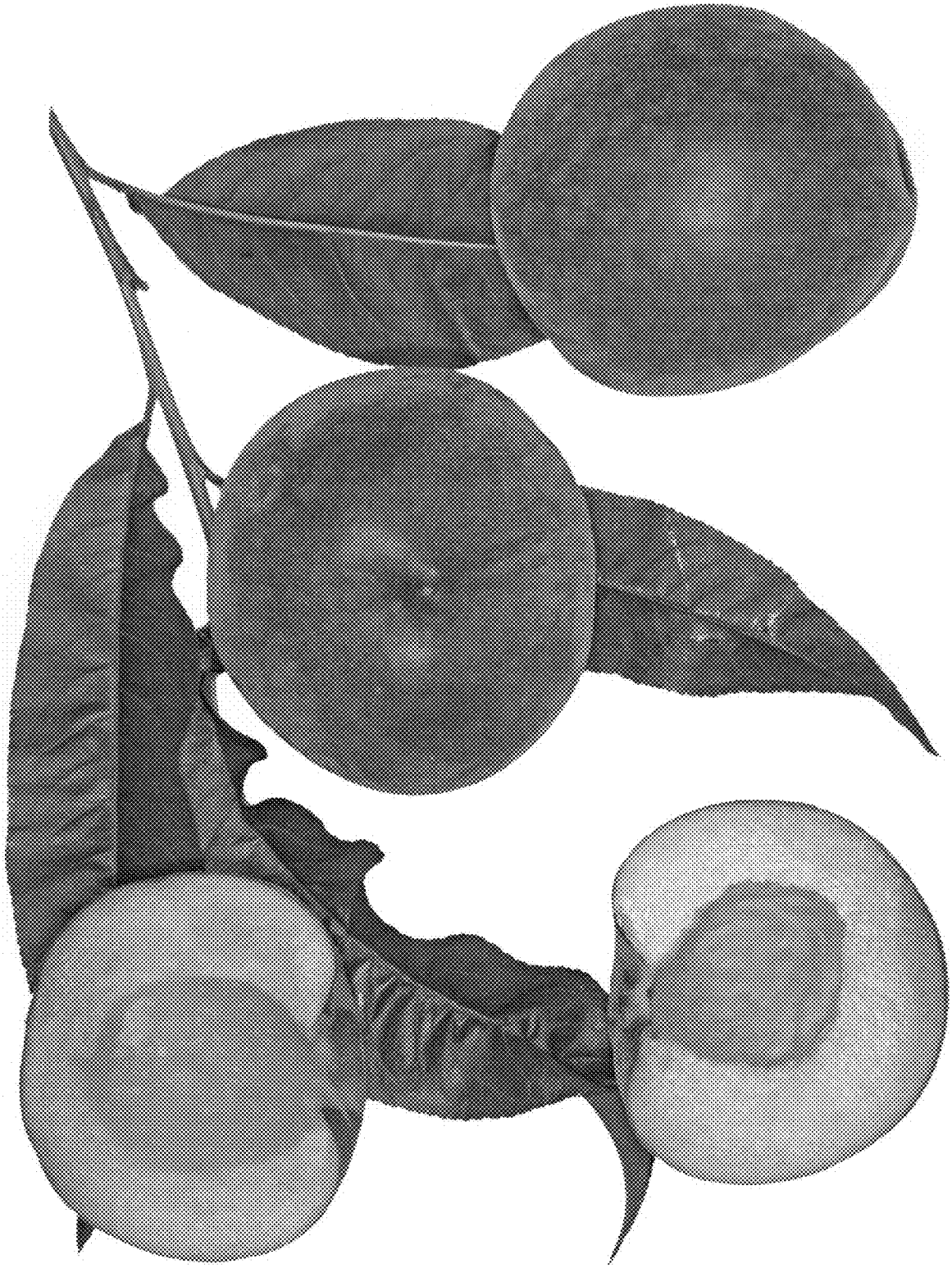

* * * * *